(12) United States Patent
Juris et al.

(10) Patent No.: US 11,938,088 B2
(45) Date of Patent: Mar. 26, 2024

(54) STRESS REDUCING, LIGHT BLOCKING, SLEEPING MASK TO IMPROVE SLEEP AND OVERALL HEALTH

(71) Applicants: Paul Mitchell Juris, Amherst, MA (US); Lisa Reynolds Juris, Amherst, MA (US)

(72) Inventors: Lisa Reynolds Juris, Amherst, MA (US); Paul Mitchell Juris, Amherst, MA (US); Sam Henry Juris, New York, NY (US)

( * ) Notice: Subject to any disclaimer, the term of this patent is extended or adjusted under 35 U.S.C. 154(b) by 26 days.

(21) Appl. No.: 17/649,756

(22) Filed: Feb. 2, 2022

(65) Prior Publication Data
US 2023/0240938 A1    Aug. 3, 2023

(51) Int. Cl.
*A61H 39/04*    (2006.01)
*A61F 9/04*    (2006.01)

(52) U.S. Cl.
CPC .............. *A61H 39/04* (2013.01); *A61F 9/04* (2013.01)

(58) Field of Classification Search
CPC .......... A61H 39/00; A61H 39/04; A61F 9/04; A61F 9/045
See application file for complete search history.

(56) References Cited

U.S. PATENT DOCUMENTS

| | | | | |
|---|---|---|---|---|
| 10,039,693 | B1* | 8/2018 | Hoffman | A61H 39/04 |
| 2009/0255026 | A1* | 10/2009 | Benner | A61F 9/04 2/12 |
| 2013/0218197 | A1* | 8/2013 | Tarumi | A63B 33/004 606/204 |
| 2019/0231595 | A1* | 8/2019 | Holtz | A61F 9/04 |

* cited by examiner

*Primary Examiner* — Todd J Scherbel
(74) *Attorney, Agent, or Firm* — Fox Rothschild LLP

(57) ABSTRACT

The stress reducing sleep mask uses a construction of layered lightweight fabrics that, when combined through the manufacturing process, effectively block light, enhance air flow, and improve comfort. The unique combination of materials and molded construction (forming) allows the mask to conform as needed around specific facial anatomical landmarks, reducing gaps that allow light filtration. This device includes a refined headband adjustment, which eliminates the need for uncomfortable buckles, or applications that create other forms of discomfort due to sleeping position or hair entanglements. An integrated acupressure device, which has been shown in clinical studies to induce calm and relaxation, helps users to fall asleep more easily. The pressure of the device can be controlled through adjustment of the headband.

18 Claims, 4 Drawing Sheets

US 11,938,088 B2

STRESS REDUCING, LIGHT BLOCKING, SLEEPING MASK TO IMPROVE SLEEP AND OVERALL HEALTH

FIELD OF THE INVENTION

The present invention relates to a novel design of sleeping mask, under the general category of sleep aids.

BACKGROUND

Sleeping masks are a popular solution for insomnia because they are relatively inexpensive when compared to products like mattresses, pillows, and blackout curtains. Sleeping masks are generally portable, they introduce no side effects, such as those experienced with pharmaceutical agents, and most importantly, they can block light, which is a significant contributor to sleep disruption.

While light-blocking is the principal concern of sleep mask users, many mask designs do not conform to anatomical facial contours, leaving significant gaps between the mask and face. These gaps allow light to filter into the eyes, reducing the efficacy of these products. Some mask configurations include padded rings that encapsulate the eye sockets to obstruct light. But these solutions tend to be bulky, create more heat, and are generally less comfortable. Furthermore, the rings may not align precisely with facial features, resulting in light penetration, or, in the case of rings which can be repositioned, becoming dislodged.

Some mask designs have a broad vertical dimension, from cheek to brow, in an effort to bar light. These, however, create a significantly greater contact surface area against the cheeks and forehead, tend to be hotter, and again, may easily become dislodged during sleep.

Retention, consequently, is a notable requirement of sleep mask users. Respondents of a survey we conducted of over 200 consumers, remarked that masks should remain fixed in place during sleep, noting a preference for products with simple and unobtrusive adjustments to retention straps. Adjustable straps were preferred over fixed elastic strings, which tend to elongate over time. Some mask designs employ plastic buckles to adjust strap length and hold the mask in place. But while these are effective in securing the mask during sleep, head pressure against the buckles can be painful, causing sleep interruptions. Some configurations place the buckles on the side of the mask, but this solution does not prevent discomfort with side sleepers.

Hook and loop fasteners are another functional adjustment option, but with the attachment point near the rear of the head, these can detach when sleepers move. Other sources of discomfort are the overlap of materials that, like buckles, create pressure points on the head, and that hair may be snagged by the fastener.

Comfort, therefore, is another critical requirement of sleep mask users. In addition to eschewing plastic buckles, our respondents noted that they preferred masks that were lightweight, soft and airy. Some mask options, which do use soft, comfortable materials, do not solve for light-penetrating gaps. Other designs that resolve these gaps, such as those employing padded rings, are heavier and hotter, and therefore, less comfortable.

Hygiene is another concern of sleeping mask consumers. Our survey respondents indicated a clear preference for masks that could be laundered without compromising the structure and durability of the product. Some higher quality masks, such as those made of silk, or cashmere, cannot be machine washed without risking damage to the material. Masks with dense foam layers, or padded rings, may not dry properly and tend to lose durability through washing. Likewise, the fixed elastic retention straps on some masks are susceptible to stretching and damage when agitated during machine washing.

Lastly, while mask designs have various degrees of success in comfortably blocking light, most respondents in our survey indicated that the principal issues preventing them from falling asleep in the first place, were stress and the failure to "turn off their brain." Except for hi-tech products, such as ambient noise generators, simple, non-pharmaceutical, cost-effective, stress-reducing solutions in sleeping masks are uncommon.

BRIEF SUMMARY OF THE INVENTION

Various embodiments of this invention include the molding of layered textiles to produce an eye shade that conforms to anatomical facial contours. These embodiments also concern the arrangement of materials to deflect light, enhance air flow, and improve comfort.

Various embodiments concern a detachable headband which may be adjusted to improve retention and comfort. The headband may be removed prior to laundering to improve durability.

An embodiment involves an apparatus designed to induce calm and relaxation, promoting sleepiness.

DETAILED DESCRIPTION OF THE INVENTION

The terminology used herein is for the purpose of describing particular embodiments only and is not intended to be limiting of the invention. The terms "comprises" or "comprising," when used in this specification, indicate the presence of stated features, elements, or components, but do not preclude the presence of one or more other features or elements.

In describing the invention, it will be understood that a number of features, or components, will be disclosed. Each of these has unique benefits, and each can also be used in conjunction with one or more, or in some cases, all of the other disclosed features or components. For the sake of clarity, therefore, this description will refrain from attempting to identify every possible combination of benefits derived from this invention. Nevertheless, this specification should be read with the understanding that such combinations are completely within the scope of the invention and claims.

In the following description, for purposes of explanation, numerous specific details are set forth in order to provide a thorough understanding of the present invention. The present disclosure is to be considered as an exemplification of the invention and is not intended to limit the invention to the specific embodiments illustrated by the figures or description below.

Figure 1:
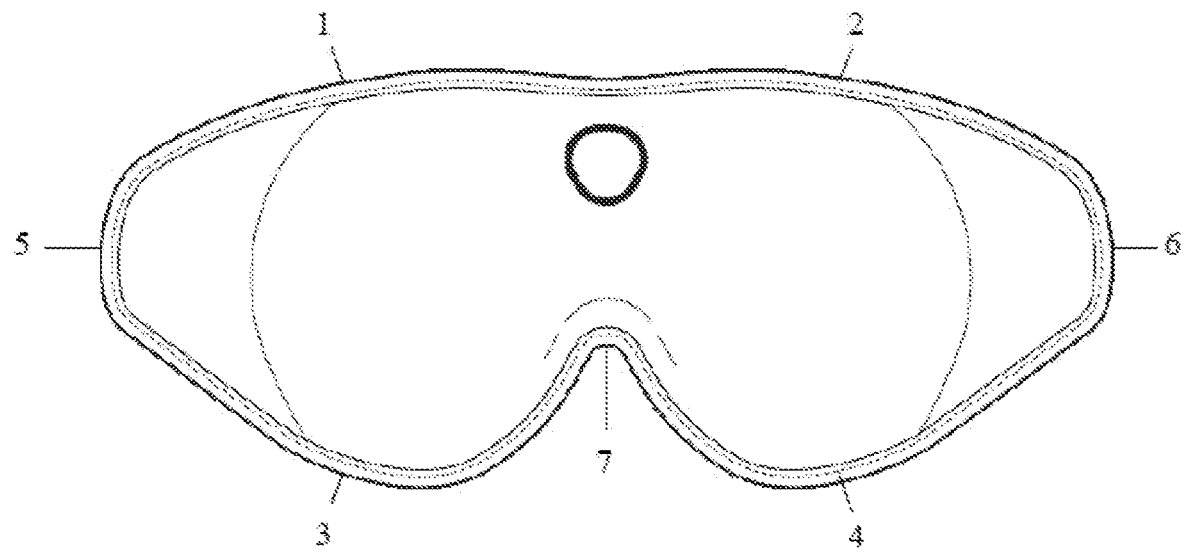
FIG. 1 shows the molded mask with anatomical contours.

The present invention will now be described by referencing the appended figures representing preferred embodiments. FIG. 1 depicts a front view of the sleeping mask according to the various embodiments of the current invention. The molded construction improves the interface between the mask and face by following the specific anatomical facial contours, above the eyebrows, along the cheek bones, and at the temples, as illustrated (1-6). The soft, pliable nose cutout (7) permits the mask to follow the contours of the nose and cheeks and eliminates voids beneath the eyes. These embodiments form a close connection to facial anatomical landmarks, when the mask is secured against the head, ensuring an uninterrupted fit for improved light blocking.

Figure 2:
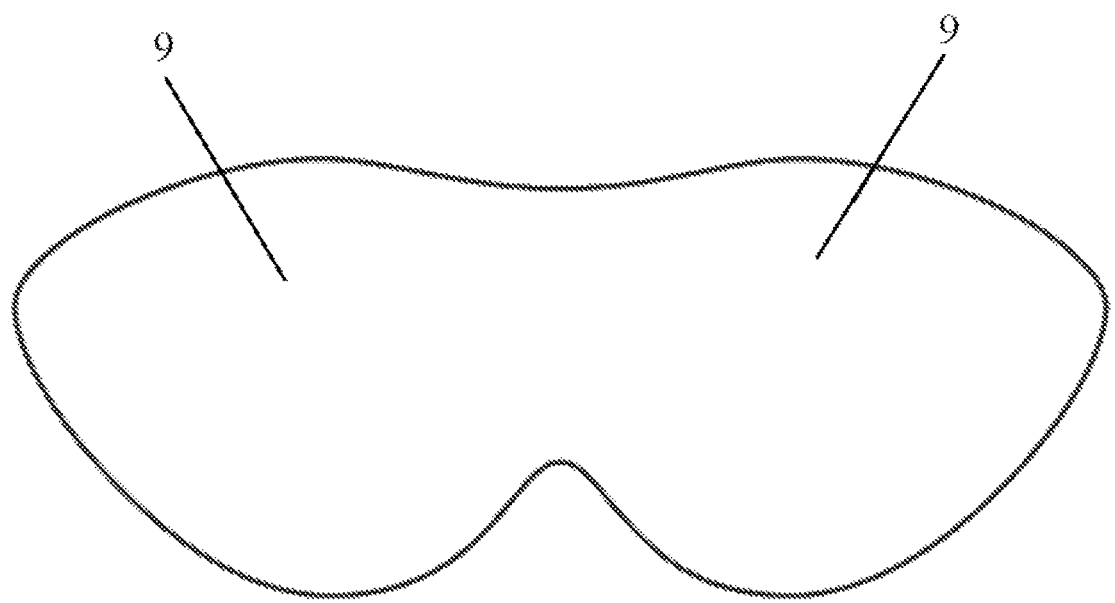
FIG. 2 illustrates the molded domes creating space in front of the eyes.

The molded construction of this invention includes embodiments seen in FIG. 2. The two dome-like voids in front of the eyes (8,9) increase the distance between the mask's surface and the eyelashes, eliminating unnecessary contact which may disrupt sleep.

Figure 3:
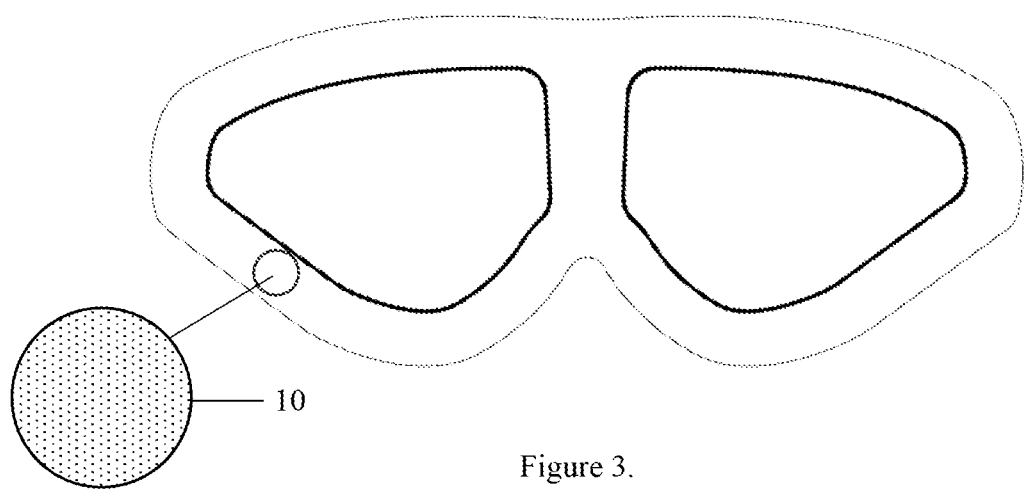
FIG. 3 presents the inner lining of the mask.

FIG. 3 provides a magnified view of the material on the facial surface of the sleeping mask. The embodiments herein (10) include a closed cell, perforated foam core, promoting breathability and light-damping, and a machine washable, 3-dimensional single mesh lining, against the face, which increases comfort.

Figure 4:
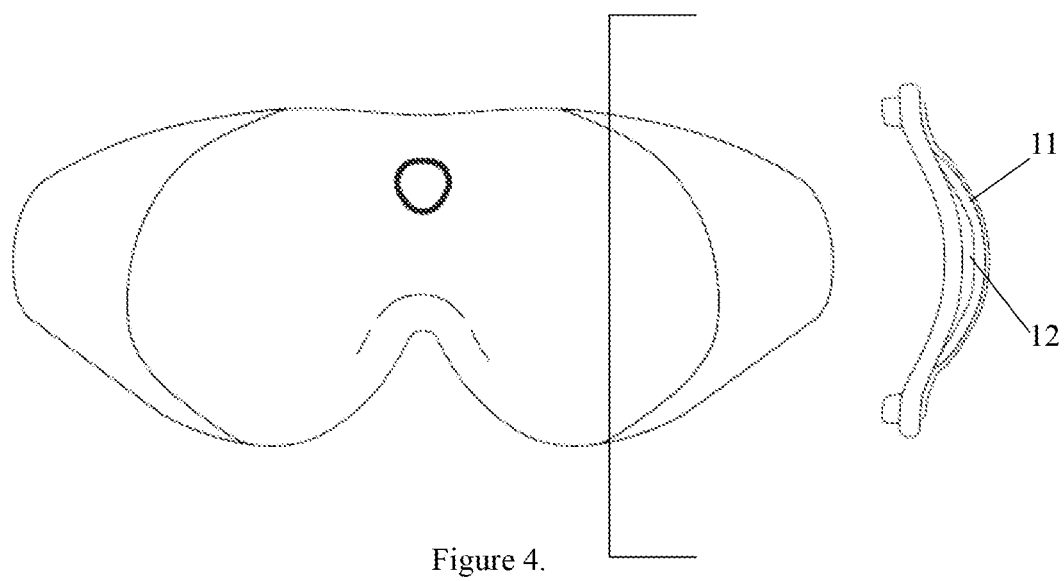
FIG. 4 displays a cutout view of the molded and layered construction of the mask.

A section view of the sleeping mask is seen in FIG. 4, illustrating the molded, layered construction of the invention. The outer, baffle layer (11) deflects and diffuses light, while an air gap (12) between the outer and inner layers reduces overall weight and increases air circulation and overall comfort. The domed curvature anterior to the eyes can also be seen in the section.

Figure 5:
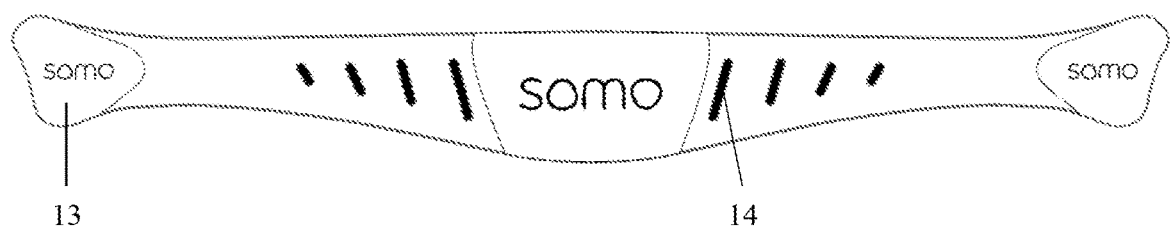
FIG. 5 shows a rear view of the detachable headband.
Figure 6:
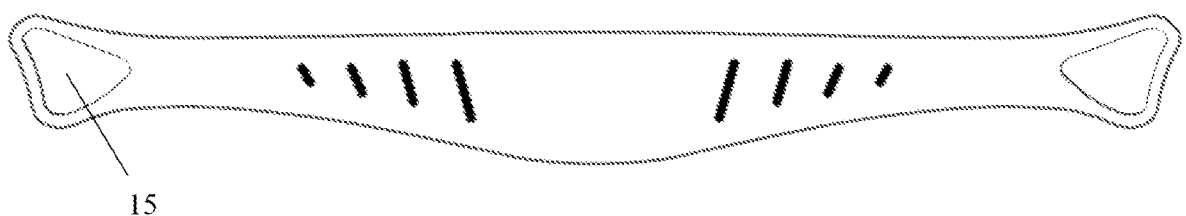
FIG. 6 illustrates the front view of the detachable headband.

An embodiment of this invention is the detachable headband (FIG. 5). Potential embodiments of this feature may include stretchable materials with nominal body, to hold shape, provide comfort and promote air permeability. Removing the headband prior to machine washing increases product durability and hygiene. The contoured ends of the headband (13) attach to the lateral corners of the eye shade, providing a secure fit. Embodiments of the diagonal cutouts in the headband (14) comprise either laser or die cuts. These cutouts permit stretching in the headband, improving adjustability, fit and comfort. The head-facing surface of the headband is illustrated in FIG. 6. A hook and loop fastener (15) is placed at the outer ends of the headband, which when wrapped around the head, interfaces with the eye shade at its lateral corners.

Figure 7:
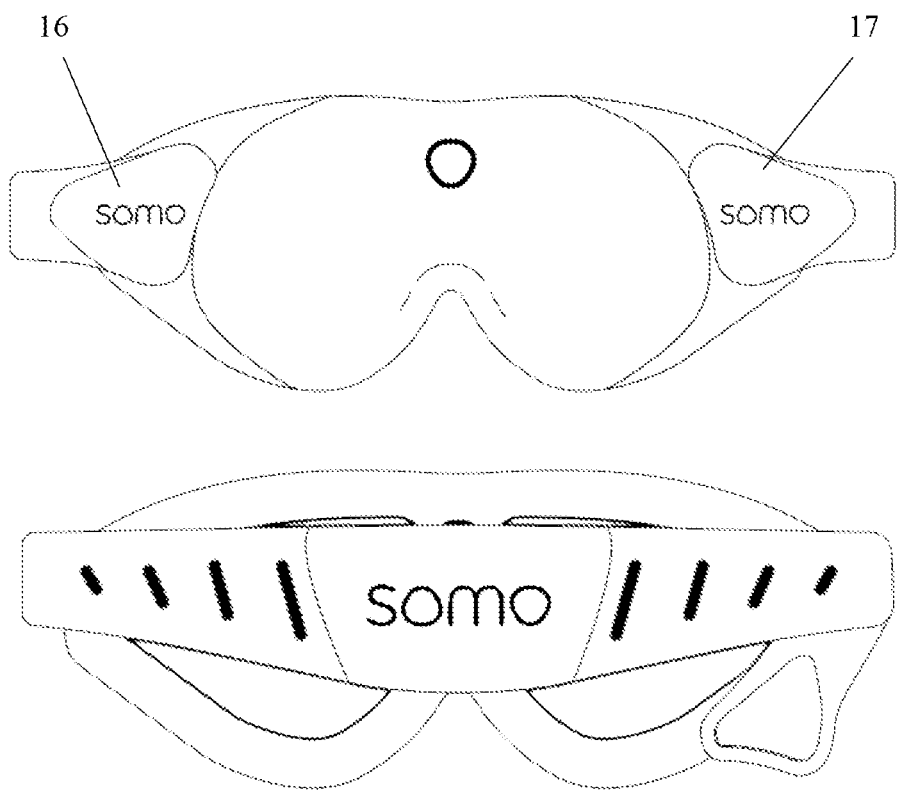
FIG. 7 displays the attachment points of the headband on the molded sleeping mask.

FIG. 7 shows the interface between the eye shade and the headband. As illustrated the hook and loop element on the headband connects with its counterpart on the eye shade at its lateral corners (16,17). The particular embodiment of this placement is to position the joined components of the sleeping mask just forward of the temples. The location of the closures, forward of the temples, is least likely to result in pressure points arising from the head pressing onto the elements, regardless of the position in which one sleeps. This position also reduces the likelihood of hair getting snagged in the closure.

Figure 8:
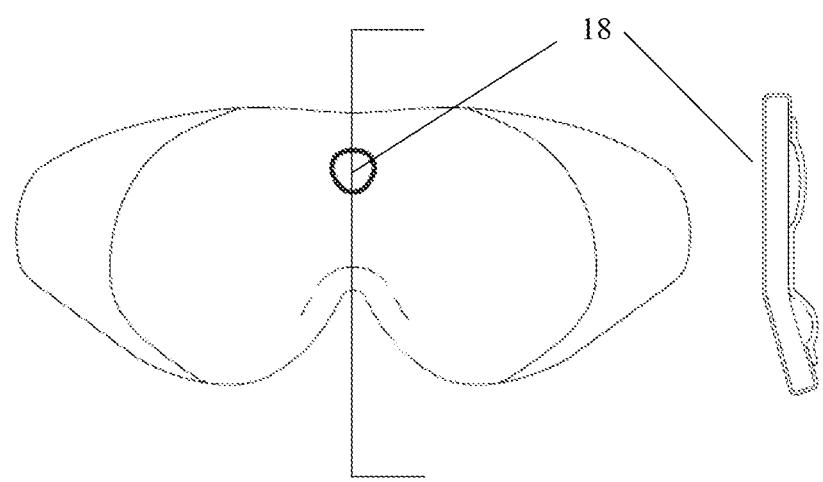
FIG. 8 presents a cutout view of the mask, highlighting the acupressure mechanism.

FIG. 8 provides a section view of the center of the invention, with particular focus on the highlighted feature (18). As illustrated on the right side of the figure, an embodiment includes a raised protuberance located above the bridge of the nose and between the eyebrows. The corresponding location on the face is an established acupressure site known as the Yin Tang point. Light compression of the Yin Tang point has been associated with stress reduction, induced calm, and improved sleep. Compression of the Yin Tang point may be modified by adjusting the headband and subsequently, the tightness of the sleeping mask.

What is claimed is:

1. A sleeping mask, comprising:
an eye shade comprising an inner layer, an outer layer configured to inhibit the passage of light through the outer layer, and a protuberance extending from the inner layer and configured to contact and exert pressure on a forehead of a user; and
a headband configured to be attached removably to the eye shade at a first and a second connection area on the eye shade, and to urge the eye shade into contact with a face and the forehead of the user; wherein:
the inner and outer layers of the eye shade define an air gap between the inner and outer layers of the eye shade;
the inner layer of the eye shade comprises a first and a second dome-shaped portion defining a respective first and a second dome-shaped void located anterior to respective eyes of the user;
the eye shade is further configured so that the first and second connection areas are located on a surface of the mask that faces away from the user when the mask is worn by the user;
the respective locations of the first and second connection areas are configured to be varied to adjust a force with which the headband urges the eye shade into contact with the face and the forehead of the user; and
the headband is unitarily formed.

2. The sleeping mask of claim 1, wherein the first and the second dome-shaped portions possess sufficient rigidity to remain spaced from eyelids and eyelashes of the user.

3. The sleeping mask of claim 1, wherein the protuberance is further configured to contact and exert pressure at a location on the forehead of the user superior to a bridge of a nose and midway between medial ends of eyebrows.

4. The sleeping mask of claim 3, wherein the protuberance is further configured to contact and exert pressure at a yin tang pressure point on the user.

5. The sleeping mask of claim 1, wherein the eye shade is further configured so that the first and the second connection areas are located forward of respective temples of the user.

6. The sleeping mask of claim 1, wherein the first and second connection areas are located at lateral corners of the eye shade.

7. The sleeping mask of claim 6, wherein the first and second connection areas are configured to be located forward of the respective temples of the user, whereby the first and second connection areas exert minimal pressure on the user regardless of a sleeping position of the user.

8. The sleeping mask of claim 1, wherein:
the eye shade further comprises hook and loop fasteners located at the first and second connection areas; and
the strap further comprises hook and loop fasteners configured to engage the hook and loop fasteners of the eye shade.

9. The sleeping mask of claim 1, wherein the outer layer is further configured to deflect and diffuse light.

10. The sleeping mask of claim 1, wherein the inner layer comprises a closed cell, perforated foam core.

11. The sleeping mask of claim 10, wherein the inner layer further comprises a three-dimensional single mesh lining mounted on the core and configured to contact the user.

12. The sleeping mask of claim 1, wherein the eye shade defines a cutout configured to permit the eye shade to conform to contours of a nose and cheeks of the user.

13. The sleeping mask of claim 1, wherein the eye shade is further configured to conform to contours of the forehead of the user.

14. The sleeping mask of claim 1, wherein the first and second dome-shaped portions are further configured to conform to respective cheekbones of the user.

15. The sleeping mask of claim 1, wherein the inner layer and the outer layer of the eyeshade are configured to move in relation to each other.

16. The sleeping mask of claim 1, wherein the eye shade is produced by a molding process.

17. The sleeping mask of claim 1, wherein the protuberance comprises a curvilinear surface configured to contact the forehead of the user.

18. The sleeping mask of claim 1, wherein the protuberance is located between the first and second dome-shaped portions.

* * * * *